(12) United States Patent
Kowarschik et al.

(10) Patent No.: US 10,779,889 B2
(45) Date of Patent: Sep. 22, 2020

(54) PLANNING SUPPORT DURING AN INTERVENTIONAL PROCEDURE

(71) Applicants: Markus Kowarschik, Nuremberg (DE); Marcus Pfister, Bubenreuth (DE)

(72) Inventors: Markus Kowarschik, Nuremberg (DE); Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 249 days.

(21) Appl. No.: 15/647,682

(22) Filed: Jul. 12, 2017

(65) Prior Publication Data
US 2018/0014884 A1   Jan. 18, 2018

(30) Foreign Application Priority Data
Jul. 14, 2016 (DE) .......................... 10 2016 212 882

(51) Int. Cl.
*G06K 9/00* (2006.01)
*A61B 34/10* (2016.01)
(Continued)

(52) U.S. Cl.
CPC .............. *A61B 34/10* (2016.02); *A61B 6/463* (2013.01); *A61B 6/504* (2013.01); *A61F 2/82* (2013.01);
(Continued)

(58) Field of Classification Search
CPC ........ A61B 2034/104; A61B 2034/105; A61B 34/10; A61B 6/463; A61B 6/504;
(Continued)

(56) References Cited

U.S. PATENT DOCUMENTS 4,983,169 A * 1/1991 Furukawa ......... A61M 25/0054
604/164.13
6,501,848 B1 * 12/2002 Carroll .................. G06T 11/006
382/128
(Continued)

FOREIGN PATENT DOCUMENTS

DE   102010041735 A1   4/2012
DE   102012215035 A1   2/2014

OTHER PUBLICATIONS

Toth, Daniel, et al. "Adaption of 3D models to 2D x-ray images during endovascular abdominal aneurysm repair." International Conference on Medical Image Computing and Computer-Assisted Intervention. Springer, Cham, 2015.*
(Continued)

*Primary Examiner* — Avinash Yentrapati
(74) *Attorney, Agent, or Firm* — Lempia Summerfield Katz LLC

(57) ABSTRACT

Methods and systems are disclosed herein for improved safer planning support during interventional procedures for inserting stents into a hollow organ of a patient by a guide device. One method includes: providing or recording a three-dimensional image data set of the hollow organ in a first position; segmentation or providing a segmentation of the three-dimensional image data set; providing or recording a two-dimensional image of the guide device introduced into the hollow organ; overlaying the three-dimensional image data set with the two-dimensional image; determining at least one corrected position of one or more section(s) of the hollow organ respectively using the overlaying of the three-dimensional image data set with the two-dimensional image; and determining the respective deformation energy of the hollow organ in the section(s) for the case of removal of the
(Continued)

guide device using the previously determined corrected position compared to the first position.

16 Claims, 6 Drawing Sheets

(51) Int. Cl.
    *G06T 7/73*      (2017.01)
    *G06T 7/11*      (2017.01)
    *A61B 6/00*      (2006.01)
    *A61F 2/82*      (2013.01)
    *A61F 2/95*      (2013.01)
    *G06T 19/20*      (2011.01)

(52) U.S. Cl.
    CPC .................. *A61F 2/95* (2013.01); *G06T 7/11* (2017.01); *G06T 7/74* (2017.01); *G06T 19/20* (2013.01); *A61B 6/5223* (2013.01); *A61B 2034/104* (2016.02); *A61B 2034/105* (2016.02); *A61F 2240/001* (2013.01); *G06T 2207/10116* (2013.01); *G06T 2207/20221* (2013.01); *G06T 2207/30101* (2013.01); *G06T 2210/41* (2013.01); *G06T 2219/2004* (2013.01); *G06T 2219/2012* (2013.01)

(58) Field of Classification Search
    CPC .... A61B 6/5223; A61F 2240/001; A61F 2/82; A61F 2/95; G06T 19/20; G06T 2207/10116; G06T 2207/20221; G06T 2207/30101; G06T 2219/2004; G06T 2219/2012; G06T 7/11; G06T 7/74
    See application file for complete search history.

(56) References Cited

U.S. PATENT DOCUMENTS

| | | | |
|---|---|---|---|
| 2004/0066955 A1* | 4/2004 | Tamez-Pena | A61B 5/418 382/128 |
| 2004/0193243 A1* | 9/2004 | Mangiardi | A61F 2/966 623/1.11 |
| 2005/0049667 A1* | 3/2005 | Arbefeuille | A61F 2/89 623/1.11 |
| 2007/0233231 A1* | 10/2007 | Krivoruchko | A61F 2/915 623/1.15 |
| 2008/0095422 A1* | 4/2008 | Suri | G06K 9/6206 382/131 |
| 2011/0235876 A1* | 9/2011 | Pfister | A61B 6/5211 382/128 |
| 2012/0082363 A1* | 4/2012 | Pfister | A61B 6/5229 382/133 |

OTHER PUBLICATIONS

Karni, Zachi, Daniel Freedman, and Craig Gotsman. "Energy-Based Image Deformation." Computer Graphics Forum. vol. 28. No. 5 . Oxford, UK: Blackwell Publishing Ltd, 2009. (Year: 2009).*
German Office Action for related German Application No. 10 2016 212 882.5 dated May 8, 2017, with English Translation.
Toth et al., "Adaption of 3D Models to 2D X-Ray Images during Endovascular Abdominal Aneurysm Repair", Siemens Healthcare GmbH, Pattern Recognition Lab, FAU, pp. 1-8 (2015).

* cited by examiner

PLANNING SUPPORT DURING AN INTERVENTIONAL PROCEDURE

The application claims the benefit of German Patent Application No. DE 10 2016 212 882.5, filed Jul. 14, 2016, which is hereby incorporated by reference in its entirety.

TECHNICAL FIELD

The disclosure relates to a method of planning support during an interventional procedure for introducing a stent into a hollow organ of a patient by a guide device and to a system for carrying out a method of this kind.

BACKGROUND

An abdominal aortic aneurysm 2 (see, e.g., FIG. 1) is an aneurysm on the abdominal aorta 1, whose extension into the leg arteries is called an iliac aneurysm. This is treated either in an open abdomen OP or in a minimally invasive manner by inserting what is known as a stent graft 3. A method of this kind is called an endovascular aneurysm repair (EVAR). Guide wires 4 and catheters are introduced into the abdominal aorta 1 via the two groins, via which wires or catheters one or more stent graft(s) 3 (e.g., a combination of a stent and an artificial blood vessel) is/are introduced. These diseases sometimes extend as far as into the leg arteries (iliac arteries 5, see FIG. 2), so sometimes the iliac stents have to be extended beyond the internal bifurcation 6. Procedures of this kind are conventionally carried out with the support of angiography systems, such as, for example, Siemens Artis zee, under radioscopy. To support interventional procedures of this kind on angiography systems, various methods are known which overlay registered pre-operative data sets, usually image data resulting from CT angiographies (CTA), on the fluoroscopy image.

The aim when inserting the stent graft is to locate the "landing zones" of the stent as far as possible in the healthy vessel wall region, but not to cover any important vessel branches in the process. Furthermore, pronounced deformations occur specifically in the highly curved iliac vessels due to the introduction of rigid instruments such as guide wires or catheters. When these instruments are removed again (e.g., once the stent graft has been released), strong restoring forces may act on the stent graft, depending on position, so the stent graft may deform or even move. A movement of this kind may impair the functioning of the stent graft or even destroy it.

In certain methods, EVAR procedures are carried out on angiography systems with fluoroscopic control. The CTA data sets are segmented in advance for this and EVAR procedures planned, wherein registration of the EVAR planning data with the angiography system may be carried out. From the article by Toth et al., "Adaption of 3D Models to 2D X-ray Images during Endovascular Abdominal Aneurysm Repair," Proc. Of the MICCAI Workshop, 2015, pp. 339-346, a method is known for determining a deformation of a vessel using overlaid image data sets.

SUMMARY AND DESCRIPTION

The scope of the present disclosure is defined solely by the appended claims and is not affected to any degree by the statements within this description. The present embodiments may obviate one or more of the drawbacks or limitations in the related art.

It is the object of the present disclosure to provide a method of planning support during an interventional procedure for introducing a stent into a hollow organ of a patient, which facilitates a risk reduction for the doctor during the subsequent performance of such procedures. Furthermore, it is an object of the disclosure to provide a device suitable for carrying out the method.

The object is achieved by a method of planning support during an interventional procedure for introducing a stent into a hollow organ of a patient by a guide device and by a system for carrying out the method.

The method of planning support for an interventional procedure for introducing a stent into a hollow organ of a patient by a guide device has the following acts: providing or recording a three-dimensional image data set of the hollow organ in a first, in particular its original, position, segmentation or providing a segmentation of the three-dimensional image data set; providing or recording an at least two-dimensional image of the guide device introduced into the hollow organ; overlaying the three-dimensional image data set with the at least two-dimensional image; determining one corrected position of one or more section(s) of the hollow organ respectively using the overlaying of the three-dimensional image data set with the at least two-dimensional image; and determining the respective deformation energy of the hollow organ in the section(s) for the case of removal of the guide device using the respective previously determined corrected position compared to the respective first position.

The method provides support that is easy to implement and quickly available to a doctor who wants to introduce a stent into the hollow organ of the patient, and therefore facilitates further action by the doctor or further decision making as to at which exact position the stent may be introduced with the lowest risk in respect of injury or accidental displacement. The basis is the assumption that the hollow organ returns to its original position following removal of the (e.g., rigid) guide device from the corrected position. It is accordingly also assumed that the greater the deformation was, the greater the "restoring forces" for reversing the deformation will be.

The method only requires the described image data, e.g., a three-dimensional image data set of the hollow organ and an at least two-dimensional data set of the guide device to be introduced or which has been introduced. Using this image data, a deformation correction and determining of the deformation energies in one or more section(s) of the hollow organ may be carried out virtually or visually. A relative estimation of the deformation energy at a plurality of points in the hollow organ may be sufficient here, because values that may be compared with each other are primarily of interest for further action by the doctor.

The segmented 3D data set, which may be obtained, for example, by a computer tomograph or a C-arm CT, may be registered, if required, with the X-ray apparatus with which the 2D image is created, for example an angiography machine.

According to one embodiment, the respective deformation energy is estimated or calculated by determining or calculating the spacings between points of the first position and corresponding points of the corrected position of the hollow organ in the section(s). Determining or calculating the spacings is a particularly simple, reliable method for estimating or calculating the deformation energy, which method may determine very exact values without great effort using the existing information.

According to a further embodiment, restoring forces are determined or estimated using the respective deformation energy. These may in turn be relative values which may be compared with each other, or accurate values are determined with the aid of absolute values that have actually been measured.

According to a further embodiment, the respective deformation energies and/or the restoring forces or their representations are displayed in the overlaid image. This kind of display provides a user with clear information which may be easily assessed and which with little effort provides him with great assistance and simplification during diagnosis and treatment. In this way, planning an interventional procedure for introducing a stent into a hollow organ may be rendered even safer for the patient.

For simple recognition of the displays, the deformation energies and/or the restoring forces are advantageously displayed color-coded, in particular by color-coded display of the guide device. A color scale, for example, may therefore be used in which red coloring of the guide device indicates a pronounced deformation while a green coloring indicates no or only a slight deformation below a, (e.g., predetermined), threshold. At points with mean deformation there is yellow coloring, transition points are indicated, for example, in a continuous color transition, alternatively also gradually. Using the displays, a doctor planning an interventional procedure may see at which point a stent causes only a slight deformation, and may plan the procedure using this information.

A system is also disclosed herein for carrying out planning support for an interventional procedure for introducing a stent into a hollow organ of a patient by a guide device. The system includes: (1) a communications device for requesting image data; (2) a storage device for storing a three-dimensional image data set of the hollow organ in a first position and an at least two-dimensional image of the guide device introduced into the hollow organ; (3) an image processing device for carrying out a segmentation of the three-dimensional image data set; (4) an overlaying device for overlaying the three-dimensional image data set with the at least two-dimensional image; and (5) a computing device for determining at least one corrected position of one or more section(s) respectively of the hollow organ using overlaying of the three-dimensional image data set with the at least two-dimensional image and for determining the deformation energy of the hollow organ in the section for the case of removal of the guide device using the previously detected corrected position compared to the first position.

The system advantageously has a display device for color-coded display of the of the previously determined deformation energy.

BRIEF DESCRIPTION OF THE DRAWINGS

Advantageous embodiments of the methods and systems are described in more detail below in the drawings using schematically illustrated exemplary embodiments, without the disclosure being limited to these exemplary embodiments thereby. In the drawings.

DETAILED DESCRIPTION

Figure 1:
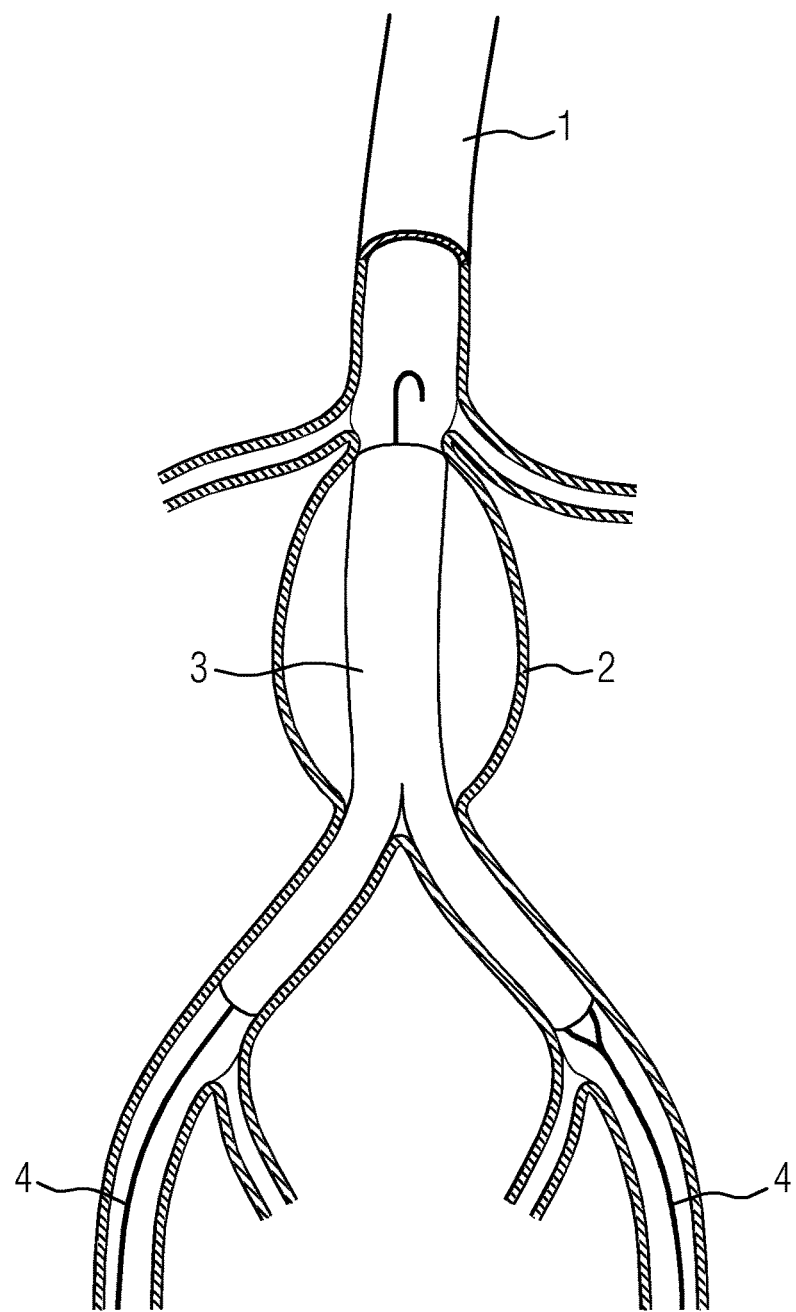
FIG. 1 depicts a view of an abdominal aortic aneurysm.
Figure 2:
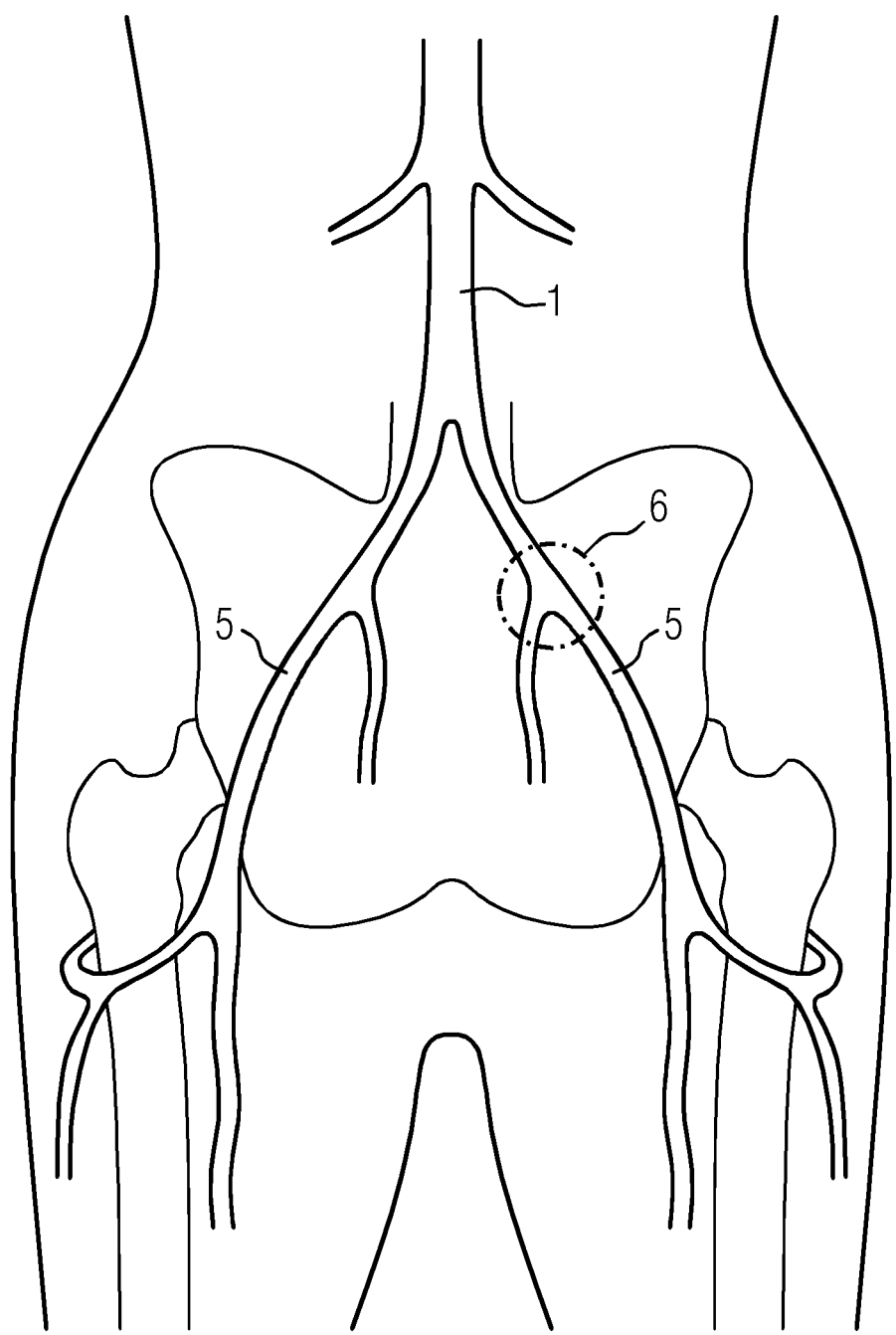
FIG. 2 depicts a view of the position of the internal bifurcation in the human body.
Figure 3:
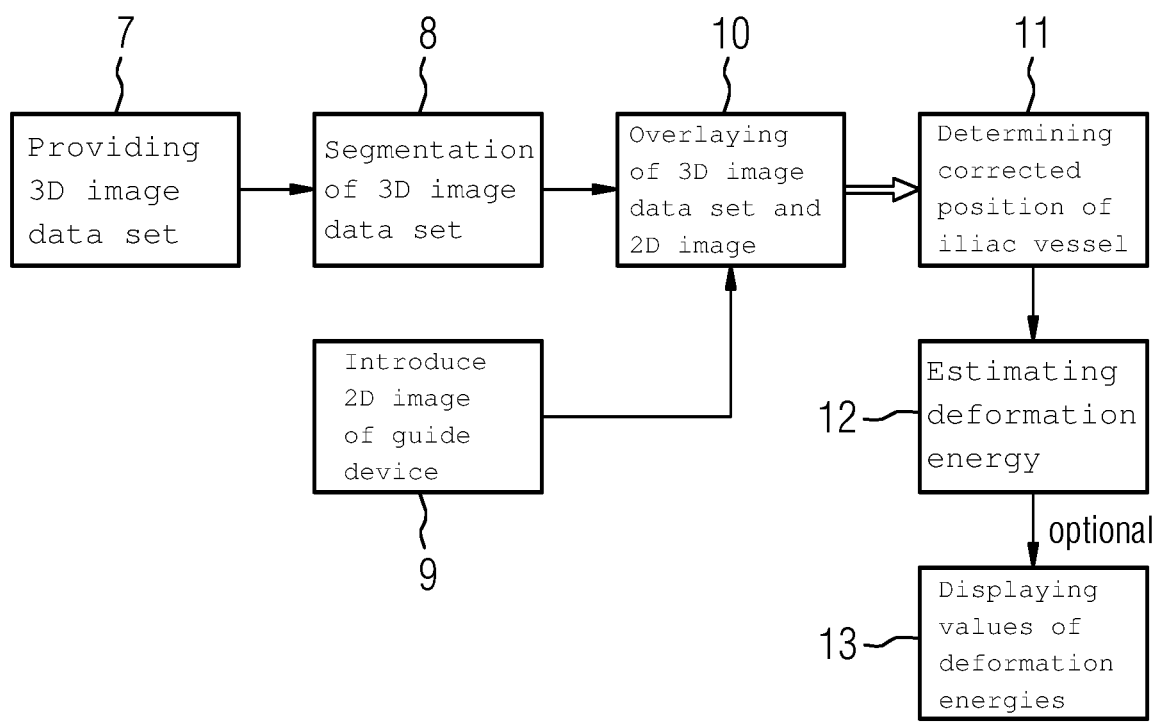
FIG. 3 depicts an example flowchart of the method.

FIG. 3 depicts a progression of the method of planning support for an interventional procedure for introducing a stent into a hollow organ of a patient by a guide device. The method is shown using the example of an iliac vessel, wherein, by way of example, the introduction of a stent graft by a guide wire is to be planned. In act 7, a three-dimensional image data set of the hollow organ (for example, iliac vessel) is provided in its original position or directly recorded. The three-dimensional image data set may be recorded, for example, by a computer tomograph or a C-arm angiography machine. The data set may also be already present in a storage device or a database and merely be retrieved. The hollow organ may also be recorded using contrast medium. The 3D data set shows a volume recording of the hollow organ.

In (optional) act 8, segmentation of the three-dimensional data set is carried out. A geometric model of the hollow organ may be obtained by way of the segmentation from the pure volume data set, which model may be easily edited and processed. Various known algorithms exist for carrying out a segmentation, then the model may include what are known as centerlines (e.g., three-dimensional central lines) and surface meshes (e.g., grids). If the three-dimensional data set is retrieved from a storage device and is already in segmented form, the act 8 may also be skipped.

In act 9, at least one two-dimensional image of a guide device introduced into the corresponding hollow organ, (e.g., guide wire), is recorded or a previously recorded image is supplied from a storage device or a database. A C-arm angiography machine, for example, is used for recording the two-dimensional image. The at least two-dimensional image includes the same hollow organ or at least the same or partially the same detail of the hollow organ. The two-dimensional image primarily shows the guide device; an ability to recognize the hollow organ is secondary. Because the guide device may have a high level of rigidity, the hollow organ is deformed. The two-dimensional image may similarly be segmented in order, for example, to better emphasize the guide wire. Segmentation of the guide device may be carried out automatically or manually.

Figure 4:
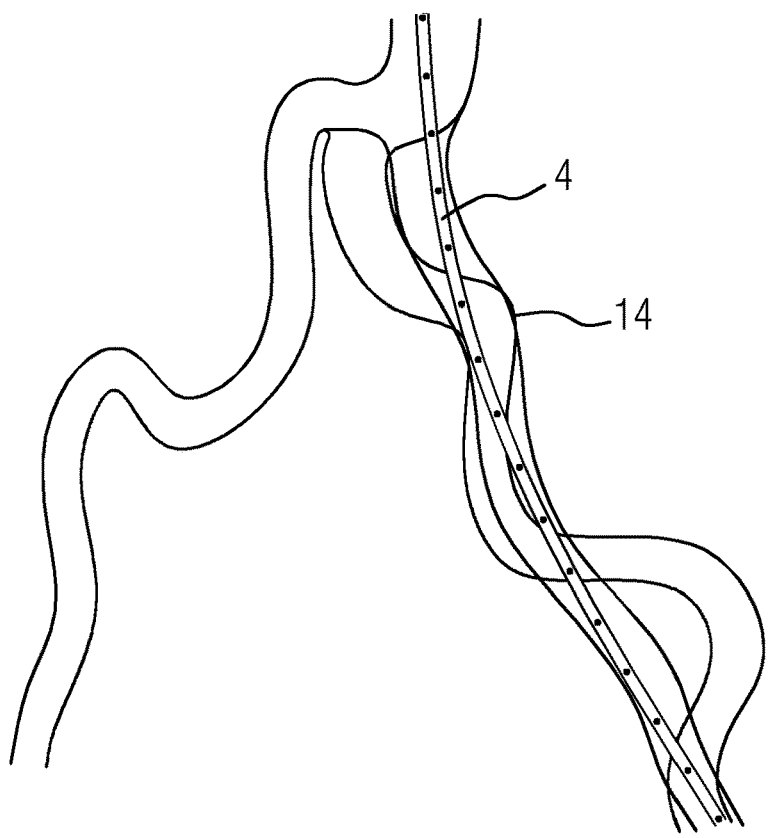
FIG. 4 depicts an example view of an overlaying of a 3D-image of a hollow organ with a 2D image of a guide wire.

In act 10, the three-dimensional image data set and the at least two-dimensional image are overlaid, for example, combined or cross-faded. To facilitate this, a (e.g., known) registration may be carried out, (e.g., a known 2D/3D or 3D/3D-registration), provided the two image data sets were not recorded by the same device, so spatially and anatomically correct overlaying of the images is possible. If the same device was used in each case, (e.g., a C-arm angiography machine), then registration may not be necessary. The segmentation may also have already been carried out before the start of the method. FIG. 4 depicts one example of overlaying. Here an iliac vessel 14 is shown which was recorded as a volume image in the original, (e.g., uninfluenced), position of the iliac vessel. A two-dimensional image of the guide wire 4 introduced into the iliac vessel is overlaid on the volume image, for example, in that the two images are partially opaquely superimposed. The position of the iliac vessel is changed as a result of the guide wire 4, wherein the hollow organ does not have to be visible on the two-dimensional image. During overlaying care is taken that the two-dimensional image is located at the appropriate spatial and anatomically correct position of the three-dimensional data set.

Figure 5:
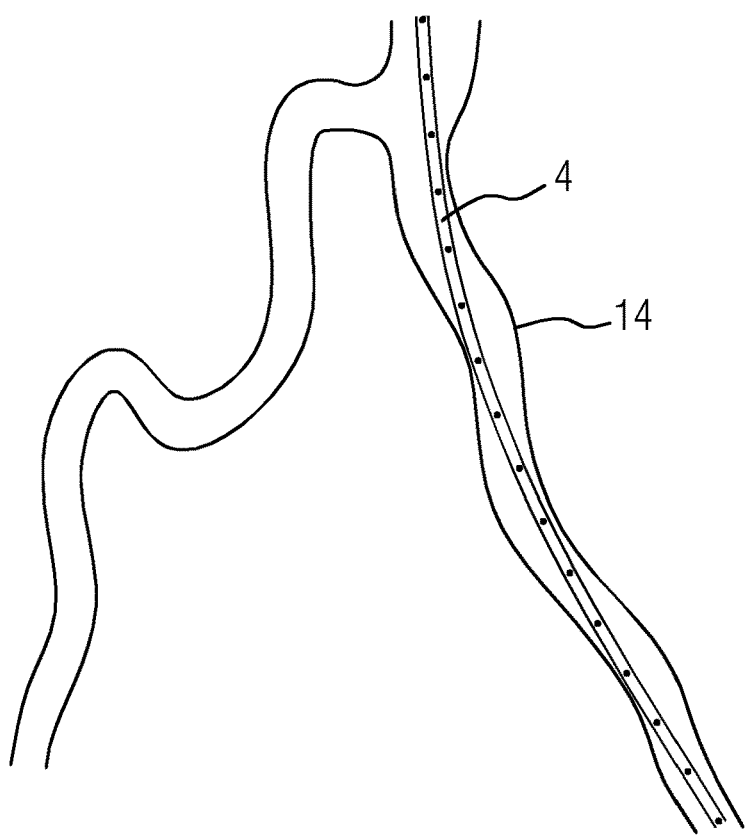
FIG. 5 depicts a view of a position of the hollow organ according to FIG. 4 corrected according to an example method.

In act 11, a corrected position of the iliac vessel is determined using the overlaying of the three-dimensional image data set with the at least two-dimensional image of the guide device. Therefore, the three-dimensional segmented model, for example, of the iliac vessel may be deformed on the two-dimensional image using the line of the guide wire, so a model of the corrected position of the iliac vessel may be created. One example of a correction of this kind is known from the article by Toth et al., "Adaption of 3D Models to 2D X-ray Images during Endovascular Abdominal Aneurysm Repair," Proc. of the MICCAI Workshop, 2015. FIG. 5 depicts one example of determination of a corrected position of the iliac vessel 14 appropriately oriented on the guide wire 4.

In act 12, the locally-acting deformation energy is estimated or determined. This is performed on the basis of the assumption that following removal of the (e.g., rigid) guide wire, the iliac vessel returns from the corrected position into its original position. The assumption that the greater the deformation was, the greater the "restoring forces" will be for reversing the deformation is also appropriate. This proportionality will be used in the present case. The relative spacing between points of the original position of the iliac vessel and points of the corrected position of the iliac vessel is therefore easily determined and the local deformation energies are then estimated or determined from these values. A large number of continuous values or equidistant values, for example, may be determined at points along the iliac vessel here. Selected sections only may also be determined.

Figure 6:
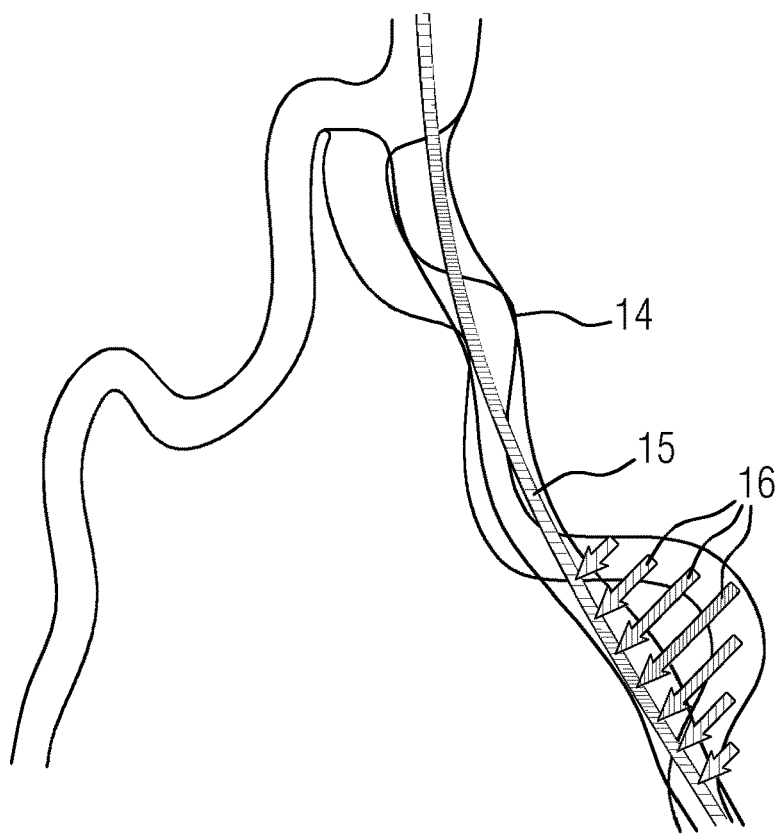
FIG. 6 depicts an example view of spacings between the original position and the corrected position of the hollow organ.
Figure 7:
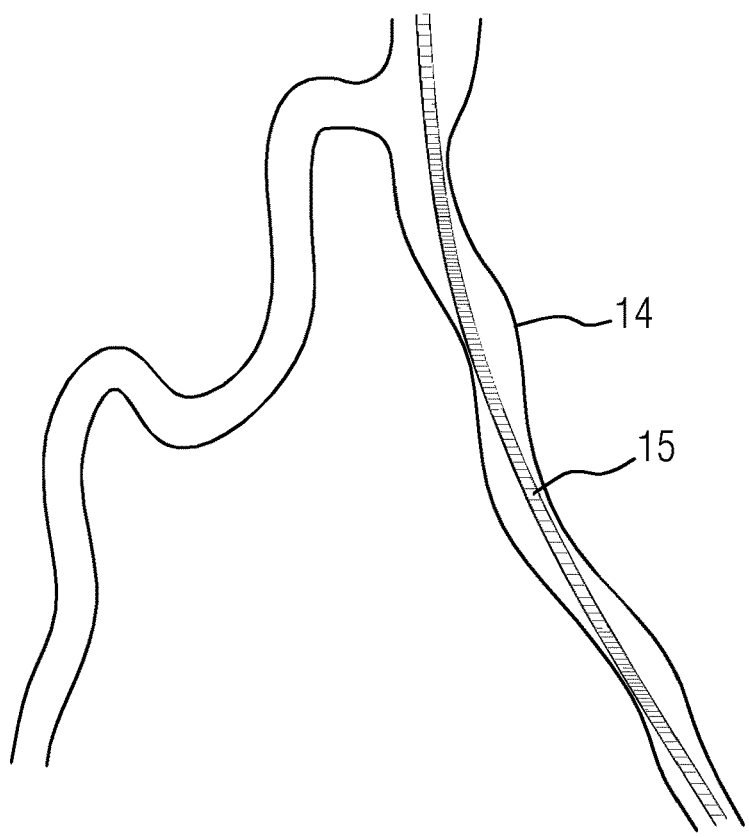
FIG. 7 depicts an example view of a color-coded display of deformation energies.

The values of the deformation energies or also just the spacings may optionally be displayed color-coded in act 13. A color scale, for example, with gradations (e.g., red, yellow, green) or a continuous color transition may therefore be displayed in the generated overlaid image. Relatively high deformation energy may therefore accordingly be displayed in red, while relatively low deformation energy may be displayed in green. Corresponding displays are depicted in FIG. 6 and FIG. 7. FIG. 6 depicts a color coding in the cross-faded image in the region of the guide wire, wherein the spacings 16 between original and corrected positions are displayed as arrows between the positions. The color-coded guide wire is superimposed in an image of the corrected position of the iliac vessel in FIG. 7. By way of the display, a doctor performing an examination of the patient may easily see at which points of the iliac vessel a strong "restoring force" will act on a potentially introduced stent graft. The doctor may modify the planned interventional procedure accordingly by choosing a "landing zone", e.g., a positioning of the stent graft at which the deformation energies or "restoring forces" are relatively low. Damage to the stent graft or undesirable slipping of the stent graft may be prevented in this way.

The method may similarly be used for other hollow organs, guide devices and stents, for example, for planning use of an aortic valve or for planning insertion of an intracranial stent in neuroradiology.

Figure 8:
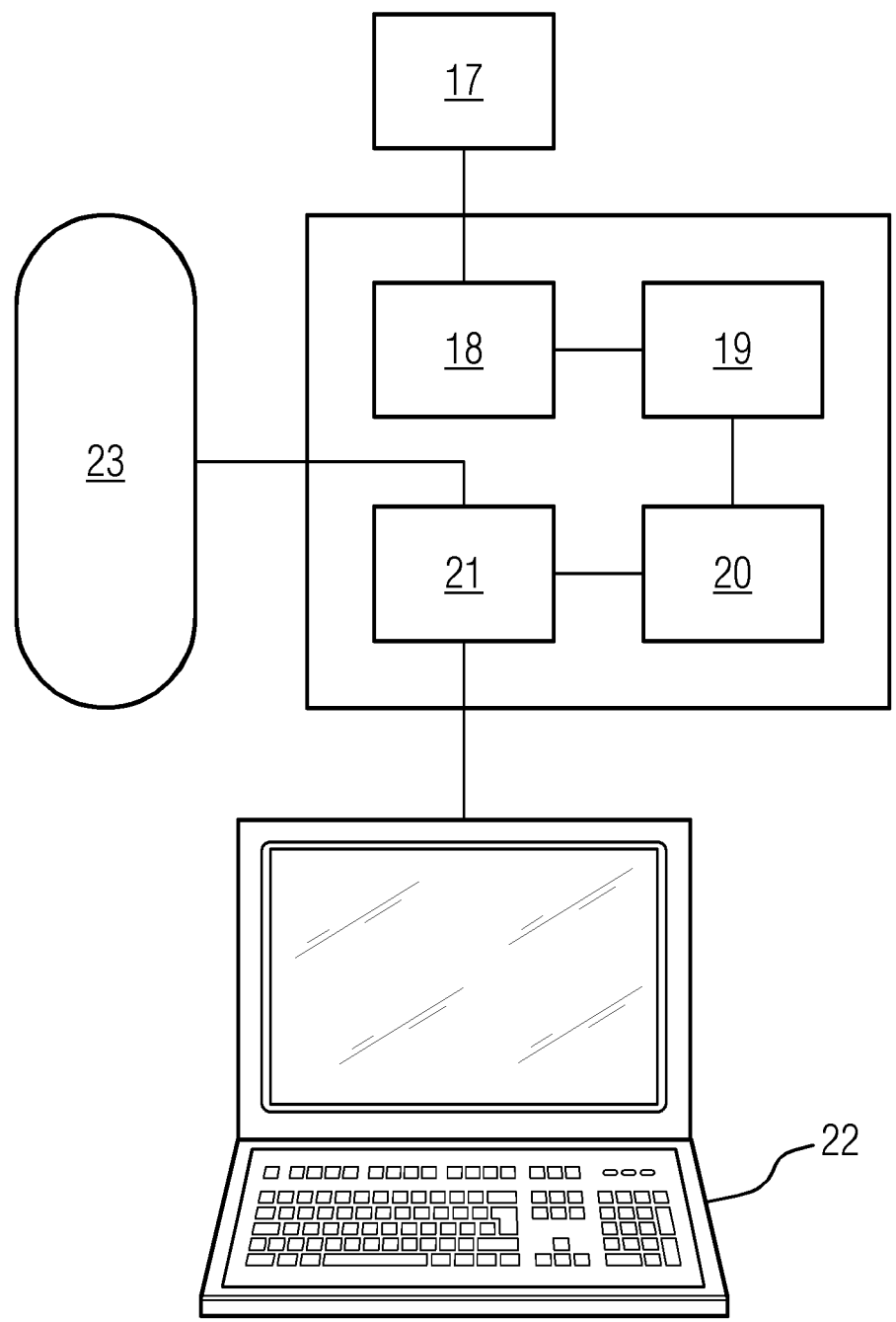
FIG. 8 depicts an example system for carrying out the method.

FIG. 8 depicts a system for carrying out the method. The system has a computing device 21 which is connected to a display device 22 for displaying image data. In addition, the system has an image processing device 19 for processing image data, an overlaying device 20 for overlaying the at least 3-dimensional image data set with the 2-dimensionalen image and a storage device 18 for storing data and image data. In addition, a communications device 17 is provided, by which the system may communicate with networks and external databases. The system also has an image recording device 23 for recording medical image data, (e.g., a C-arm angiography machine), by which two-dimensional images may be recorded.

The background idea of the method is the estimation of the restoring forces potentially acting on a stent (e.g., graft) for a hollow organ using the deformation of the hollow organ, which deformation is determined by a 2D3D-overlaying of before-after image data. The advantage of the method consists in estimating the restoring forces potentially acting on a stent by way of recognition of an introduced guide device without the stent itself being introduced into the hollow organ, or before the stent is introduced for this purpose. The doctor is therefore capable of choosing regions with as little deformation as possible for setting down stents, for example iliac stents, in order to thus prevent bending or movement of the stent.

The disclosure may be summarized in brief as follows. The following acts are provided for improved and, for the patient, safer planning support during interventional procedures for inserting stents into a hollow organ of a patient by a guide device: providing or recording a three-dimensional image data set of the hollow organ in a first, in particular its original, position; segmentation or providing a segmentation of the three-dimensional image data set; providing or recording an at least two-dimensional image of the guide device introduced into the hollow organ; overlaying the three-dimensional image data set with the at least two-dimensional image; determining at least one corrected position of one or more section(s) of the hollow organ respectively using the overlaying of the three-dimensional image data set with the at least two-dimensional image; and determining the respective deformation energy of the hollow organ in the section(s) for the case of removal of the guide device using the previously determined corrected position compared to the first position.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method of planning support for an interventional procedure for introducing a stent into a hollow organ of a patient by a guide device, the method comprising:
   providing or recording a three-dimensional image data set of the hollow organ in a first position;
   segmenting or providing a segmentation of the three-dimensional image data set;
   providing or recording an at least one two-dimensional image of the guide device introduced into the hollow organ;
   overlaying the three-dimensional image data set with the at least one two-dimensional image to provide an overlaid image;
   determining at least one corrected position of one or more sections of the hollow organ respectively using the overlaid image; and
   determining a respective deformation energy of the hollow organ in the one or more sections for a case of removal of the guide device and placement of the stent into the hollow organ using the at least one determined corrected position compared to the first position, prior to the removal of the guide device and the placement of the stent.

2. The method of claim 1, wherein the first position is an original position.

3. The method of claim 1, wherein the respective deformation energy is estimated by determining or calculating spacings between the first position and the corrected position of the hollow organ in the one or more sections.

4. The method of claim 3, wherein the respective deformation energies or a representation of the deformation energies are displayed in the overlaid image.

5. The method of claim 4, wherein the deformation energies are displayed color-coded, wherein a first deformation energy of the deformation energies is depicted by a first color and a second, different deformation energy of the deformation energies is depicted by a second, different color.

6. The method of claim 4, wherein the deformation energies are displayed color-coded by a display device.

7. The method of claim 1, wherein the respective deformation energies or a representation of the deformation energies are displayed in the overlaid image.

8. The method of claim 7, wherein the deformation energies are displayed color-coded, wherein a first deformation energy of the deformation energies is depicted by a first color and a second, different deformation energy of the deformation energies is depicted by a second, different color.

9. The method of claim 7, wherein the deformation energies are displayed color-coded by a display device.

10. A system for carrying out planning support for an interventional procedure for introducing a stent into a hollow organ of a patient by a guide device, the system comprising:
    a communications device configured to request image data;
    a storage device configured to store a three-dimensional image data set of the hollow organ in a first position and an at least one two-dimensional image of the guide device introduced into the hollow organ;
    an image processing device configured to carry out a segmentation of the three-dimensional image data set;
    an overlaying device configured to overlay the three-dimensional image data set with the at least one two-dimensional image to provide an overlaid image; and
    a computing device configured to determine at least one corrected position of one or more sections respectively of the hollow organ using the overlaid image, and to determine a deformation energy of the hollow organ in the section for a case of removal of the guide device and placement of the stent into the hollow organ using the at least one determined corrected position compared to the first position, prior to the removal of the guide device and the placement of the stent.

11. The system of claim 10, further comprising:
    a display device configured to provide a color-coded display of the determined deformation energy.

12. The system of claim 11, further comprising:
    an image recording device configured to record the at least one two-dimensional image.

13. The system of claim 12, wherein the image recording device is an angiography machine.

14. The system of claim 10, further comprising:
    an image recording device configured to record the at least one two-dimensional image.

15. The system of claim 14, wherein the image recording device is an angiography machine.

16. The method of claim 1, further comprising:
    determining an optimal position for the placement of the stent based on the determined deformation energies, wherein the optimal position is based on a relatively low determined deformation energy of the determined deformation energies.

* * * * *